United States Patent
Lee et al.

(10) Patent No.: US 8,547,890 B2
(45) Date of Patent: Oct. 1, 2013

(54) SYSTEM AND METHOD FOR POWER SAVING FOR IN-BODY AND ON-BODY COMMUNICATION

(75) Inventors: Cheolhyo Lee, Daejeon (KR); Hong Soon Nam, Daejeon (KR); Hyung Soo Lee, Daejeon (KR); Jae Young Kim, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 248 days.

(21) Appl. No.: 12/960,396

(22) Filed: Dec. 3, 2010

(65) Prior Publication Data

US 2011/0134820 A1    Jun. 9, 2011

(30) Foreign Application Priority Data

Dec. 4, 2009 (KR) .................. 10-2009-0119958

(51) Int. Cl.
  *H04W 52/02*    (2009.01)
(52) U.S. Cl.
  USPC ......................................... 370/311
(58) Field of Classification Search
  USPC .............................. 370/254–340
  See application file for complete search history.

(56) References Cited

U.S. PATENT DOCUMENTS

| | | | |
|---|---|---|---|
| 7,447,526 B2 * | 11/2008 | Kim et al. | 455/574 |
| 7,522,639 B1 * | 4/2009 | Katz | 370/503 |
| 2007/0008915 A1 | 1/2007 | Kim et al. | |
| 2009/0022078 A1 * | 1/2009 | Patterson et al. | 370/311 |

FOREIGN PATENT DOCUMENTS

| | | |
|---|---|---|
| KR | 10-2006-0130356 A | 12/2006 |
| KR | 10-0867542 B1 | 11/2008 |

OTHER PUBLICATIONS

Sha Liu et al., "CMAC: An Energy Efficient MAC Layer Protocol Using Convergent Packet Forwarding for Wireless Sensor Networks", SECON 2007, 2007.

Anis Koubaa et al., "A Time Division Beacon Scheduling Mechanism for IEEE 802.15.4/Zigbee Cluster-Tree Wireless Sensor Networks", 19th Euromicro conference on real-time systems, 2007.

* cited by examiner

*Primary Examiner* — Ayaz Sheikh
*Assistant Examiner* — Debebe Asefa

(57) ABSTRACT

A system for power saving in communication with a plurality of sensor apparatuses that are located in-body or on-body to sense bioinformation, a management apparatus that performs synchronization by transmitting a beacon signal to the plurality of sensors at each predetermined period, and a sensor apparatus that includes a sensor receiving a first beacon signal, grasps how much time remains until the second beacon signal is received when the sensor is activated to sense the bioinformation, and determines the operation state of the sensor based on the grasped time are provided.

12 Claims, 6 Drawing Sheets

SYSTEM AND METHOD FOR POWER SAVING FOR IN-BODY AND ON-BODY COMMUNICATION

CROSS-REFERENCE TO RELATED APPLICATION

This application claims priority to and the benefit of Korean Patent Application No. 10-2009-0119958 filed in the Korean Intellectual Property Office on Dec. 4, 2009, the entire contents of which are incorporated herein by reference.

BACKGROUND OF THE INVENTION (a) Field of the Invention

The present invention relates to a system and method for power saving for in-body and on-body communication.

(b) Description of the Related Art

A sensor apparatus that is located in-body and on-body has an external management apparatus and a short communication distance as compared to a general communication environment, and transmits biosensor information to the external management apparatus over the short communication distance.

Functions of a communication apparatus that collects sensor information in-body and on-body can be largely divided into a biosensor obtaining function and a wireless communication function. These functions are similar to a wireless communication apparatus used in a sensor network.

Since the wireless communication apparatus for a sensor network transmits a small amount of data at a low speed, it can be miniaturized and a battery can be used for a long time without a separate power source.

In other words, since the battery is used even though the sensor apparatus is implanted in-body and is mounted on-body, it is important to use the battery for as long a time as possible. However, when the sensor apparatus is mainly operated by the battery and communication is frequent and intermittent, since the apparatus is unnecessarily operated, there is a problem in that the lifetime of the battery is short.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a system and method for power saving for in-body and on-body communication.

In order to achieve the above objects, an exemplary embodiment according to the present invention provides a method for power saving in communication between a plurality of sensor apparatuses that are located in-body or on-body to collect bioinformation, and an external management apparatus, including:

connecting a first sensor apparatus to the management apparatus in a state in which the first sensor apparatus monitors a living body; registering an activation period of the first sensor apparatus; changing the operation state of the first sensor apparatus from the activation state to the deactivation state and operating a timer; stopping the operation of the timer when the activation period is completed during the operation of the timer and changing the operation state from the deactivation state to the activation state; detecting a packet for a beacon period in the activation state; and transmitting the bioinformation to the management apparatus at the time when the packet is included and changing the operation state of the first sensor apparatus back to the deactivation state.

Another exemplary embodiment according to the present invention provides a method for power saving in communication between a plurality of sensor apparatuses that are located in-body or on-body to collect bioinformation, and an external management apparatus, including:

receiving a first beacon signal from the management apparatus; detecting a packet in a state in which the sensor apparatus is activated to collect bioinformation; calculating remaining time until a second beacon signal corresponding to a next signal of a first beacon signal is received, based on a specific field included in the detected packet; comparing the remaining time with a time that is a sum of a time needed to change the sensor apparatus from the activation state into the deactivation state in which the bioinformation is not collected and a time needed to change the sensor apparatus from the activation state to the deactivation state; and determining the operation state of the sensor apparatus based on the comparison result.

Yet another exemplary embodiment according to the present invention provides a system for power saving in communication with a plurality of sensor apparatuses that are located in-body or on-body to sense bioinformation, including:

a management apparatus that performs synchronization by transmitting a beacon signal to the plurality of sensors at each predetermined period; and a sensor apparatus that includes a sensor receiving a first beacon signal, grasps how much time remains until the second beacon signal is received when the sensor is activated to sense the bioinformation, and determines the operation state of the sensor based on the grasped time.

DETAILED DESCRIPTION OF THE EMBODIMENTS

Figure 1:
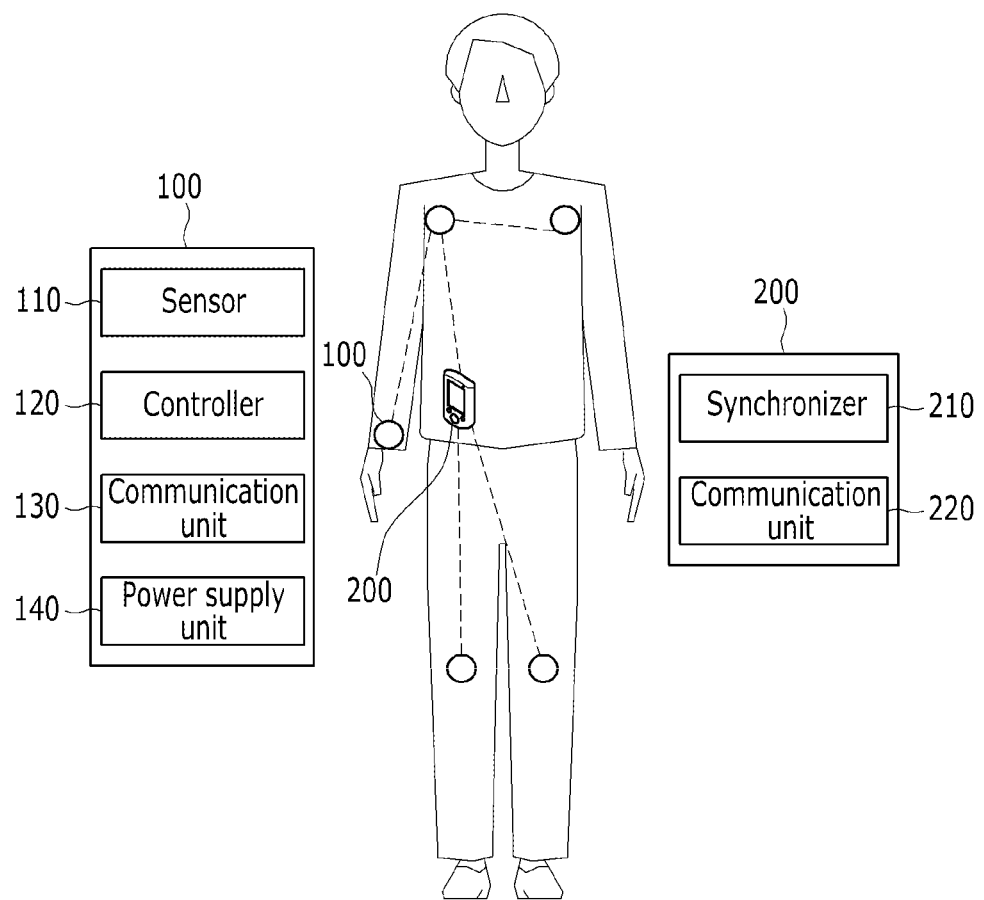
FIG. 1 is a diagram showing an environment in which a system for power saving for in-body or on-body communication according to an exemplary embodiment of the present invention is applied.

In the following detailed description, only certain exemplary embodiments of the present invention have been shown and described, simply by way of illustration. As those skilled in the art would realize, the described embodiments may be modified in various different ways, all without departing from the spirit or scope of the present invention. Accordingly, the drawings and description are to be regarded as illustrative in nature and not restrictive. Like reference numerals designate like elements throughout the specification.

In the specification, unless explicitly described to the contrary, the word "comprise" and variations such as "comprises" or "comprising" will be understood to imply the inclusion of stated elements but not the exclusion of any other elements.

In the specification, a terminal may designate a mobile station (MS), a mobile terminal (MT), a subscriber station (SS), a portable subscriber station (PSS), user equipment (UE), an access terminal (AT), etc., and may include the entire or partial functions of the mobile station, mobile terminal, subscriber station, portable subscriber station, user equipment, access terminal, etc.

Hereinafter, a system and method for power saving for in-body and on-body communication according to a method of an exemplary embodiment of the present invention will be described in detail with reference to the accompanying drawings.

First, apparatuses used for in-body and on-body communication are classified into a medical apparatus or a non-medical apparatus that collect medical or non-medical information.

The medical apparatus is connected to a sensor to measure biosignals in-body and on-body, such that it collects medical information based on the measured biosignals and uses the collected medical information for medical examination.

The non-medical apparatus is used to collect information on a body state such as acceleration, motion, etc., that is, the non-medical information, wherein the non-medical information is used for purposes of health aid or entertainment for exercise amount monitoring, entertainment, etc.

In other words, the apparatuses used for in-body and on-body communication are attached in-body and on-body to perform the communication with other apparatuses, for example, a terminal. At this time, when the apparatuses transmit the collected information to the terminal through a wireless network, they should consider factors such as transmission speed and periodicity, importance, transmission delay, regulation of information, etc. The distance between the apparatuses and the terminal, that is, the transmission distance, is considerably short on the order of several meters. Therefore, among the apparatuses used for in-body and on-body communication, that is, when a sensor apparatus is implanted in-body or otherwise, is mounted on-body, the sensor apparatus is supplied with power by using a power supply apparatus such as a battery included therein.

A system for power saving of the apparatuses used for in-body and on-body communication will be described in detail with reference to FIG. 1.

FIG. 1 is a diagram showing an environment in which a system for power saving for in-body or on-body communication according to an exemplary embodiment of the present invention is applied.

Referring to FIG. 1, the system for power saving includes a plurality of sensor apparatuses 100 and a management apparatus 200. Herein, the plurality of sensor apparatuses 100 are connected to the management apparatus 200 through a wireless network.

Each of the plurality of sensor apparatuses 100 is implanted in-body or attached on-body to monitor a living body, and transmits the monitoring results to the management apparatus 200. For this purpose, each of the plurality of sensor apparatuses 100 includes a sensor 110, a controller 120, a communication unit 130, and a power supply unit 140.

The sensor 110 senses bioinformation including body heat, pulse, and blood pressure of a human body at a predetermined period to generate biosignals including bioinformation. Herein, the operation state of each sensor 110 is divided into an activation state or a deactivation state. The activation state is a state where power is supplied so that the sensor 110 can sense the bioinformation, and the deactivation state is to minimize unnecessary power consumption including an RF transmitting/receiving function, and if necessary, can control the operation of the sensor 110. In other words, the operation state of the sensor 110 corresponds to the operation state of the sensor apparatus 100.

The controller 120 controls the operation state of the sensor 110 according to whether a beacon signal is received.

In detail, the controller 120 generates a packet corresponding to the biosignal in a beacon period based on a received beacon signal B. Herein, the beacon period is a period when the beacon signal B is received, after which it receives a next beacon signal. In addition, the generated packet includes a time stamp field corresponding to a relative value that shows when the biosignal including the bioinformation is transmitted to the management apparatus 200 at any time in the beacon period.

When the sensor 110 is changed from the deactivation state to the activation state, the controller 120 grasps how much time remains until the next beacon signal B is received and determines whether the sensor 110 is again changed into the deactivation state based on the grasped result.

The controller 120 compares the remaining time T until the next beacon signal B is received and a time until the operation state of the sensor 110 is changed, and controls the operation state of the sensor 110 based on the comparison results.

The controller 120 changes the operation state of the sensor 110 to the deactivation state when the remaining time T is longer than a time that is a sum of a time needed to change the operation state of the sensor 110 from the deactivation state to the activation state and a time needed to change the operation state of the sensor 110 from the deactivation state to the activation state. On the other hand, when the remaining time T is short, the controller 120 maintains the operation state of the sensor 110 in the activation state.

The communication unit 130 receives the beacon signal B from the management apparatus 200 at each predetermined time period and transmits a packet generated by the controller 120 to the management apparatus 200.

The power supply unit 140 supplies power to the sensor apparatus 100 by using a battery.

In detail, the power supply unit 140 supplies power to the sensor 110 when the operation state of the sensor 110 is the activation state. On the other hand, when the operation state of the sensor 110 is the deactivation state, minimal power corresponding to that which can be supplied with the control signal from the management apparatus 200 is supplied.

As described above, each of the plurality of sensor apparatuses 100 uses the beacon signal B and the packet to reduce time required to maintain an unnecessary activation state, thereby making it possible to reduce power consumption.

Next, the management apparatus 200 includes a synchronizer 210 and a communication unit 220.

The synchronizer 210 generates the beacon signal B in a predetermined time period and receives the packet corresponding to the biosignal including the bioinformation in the beacon period. Herein, the packet includes a time stamp field corresponding to a relative value that shows when the biosignal including the bioinformation is received at any time in the beacon period that is a predetermined time period of the beacon signal B.

The communication unit 220 transmits the beacon signal B generated in the synchronizer 210 to the plurality of sensor apparatuses 100 to perform synchronization with the plurality of sensor apparatuses 100. In addition, the communication unit 220 receives the packet corresponding to the beacon signal B. At this time, the packet includes the biosignal including the bioinformation.

The plurality of sensor apparatuses 100 may be deeply positioned in the body, or may be positioned at the front and back of a body that does not secure a line of sight (LOS). At this time, when the plurality of sensor apparatuses 100 communicate with the management apparatus 200, radio wave attenuation occurs, such that there is a case where the communication is difficult. For this reason, the plurality of sensor apparatuses 100 and the management apparatus 200 according to the exemplary embodiment of the present invention are more suitable to form the network using a tree topology rather than a star topology.

Next, the operation timing of the plurality of sensor apparatuses 100 according to the exemplary embodiment of the present invention will be described in detail with reference to FIG. 2.

Figure 2:
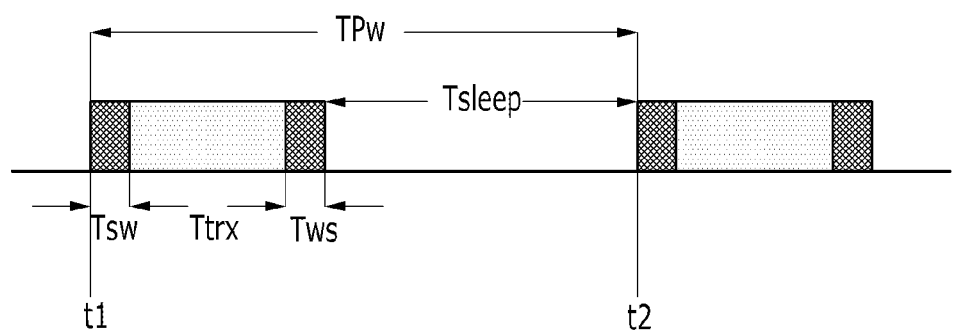
FIG. 2 is a diagram showing operation timing of the sensor apparatus according to the exemplary embodiment of the present invention.

FIG. 2 is a diagram showing the operation timing of the sensor apparatus according to the exemplary embodiment of the present invention.

First, when each of the plurality of sensor apparatuses 100 is changed from the activation state to the deactivation state or from the deactivation state to the activation state, a predetermined changing time is needed. Next, the operation timing of one of the plurality of sensor apparatuses 100 will be described.

Referring to FIG. 2, the sensor apparatus 100 changes the sensor 110 from the deactivation state to the activation state and from the activation state to the deactivation state in a predetermined time period. In other words, the sensor apparatus 100 according to the exemplary embodiment of the present invention defines the predetermined time period, that is, the activation period TPw, from the time t1 when the sensor 110 is changed from the deactivation state to the activation state to the time t2 when the sensor 110 is again changed from the deactivation state to the activation state.

The sensor 110 changes the operation state according to the control signal transmitted from the controller 120 for a predetermined time TPw.

In detail, when the first control signal is received, the sensor 110 consumes the first time Tsw to change the operation state from the deactivation state to the activation state to correspond to the first control signal. The first control signal is a control signal to change the operation of the sensor 110 from the deactivation state to the activation state. Next, the sensor 110 is maintained in the activation state for a second time Trx.

When the second control signal is received, the sensor 110 consumes a third time Tws to change the operation state from the activation state to the deactivation state to correspond to the second signal. The second control signal is a control signal to change the operation of the sensor 110 from the activation state to the deactivation state. Next, the sensor 110 is maintained in the deactivation state for a fourth time Tsleep.

Next, a format of the packet including the time stamp field when the beacon signal is transmitted in a predetermined time period in order to perform synchronization with the plurality of sensor apparatuses 100 with the network in the management apparatus 200 will be described in detail with reference to FIG. 3.

Figure 3:
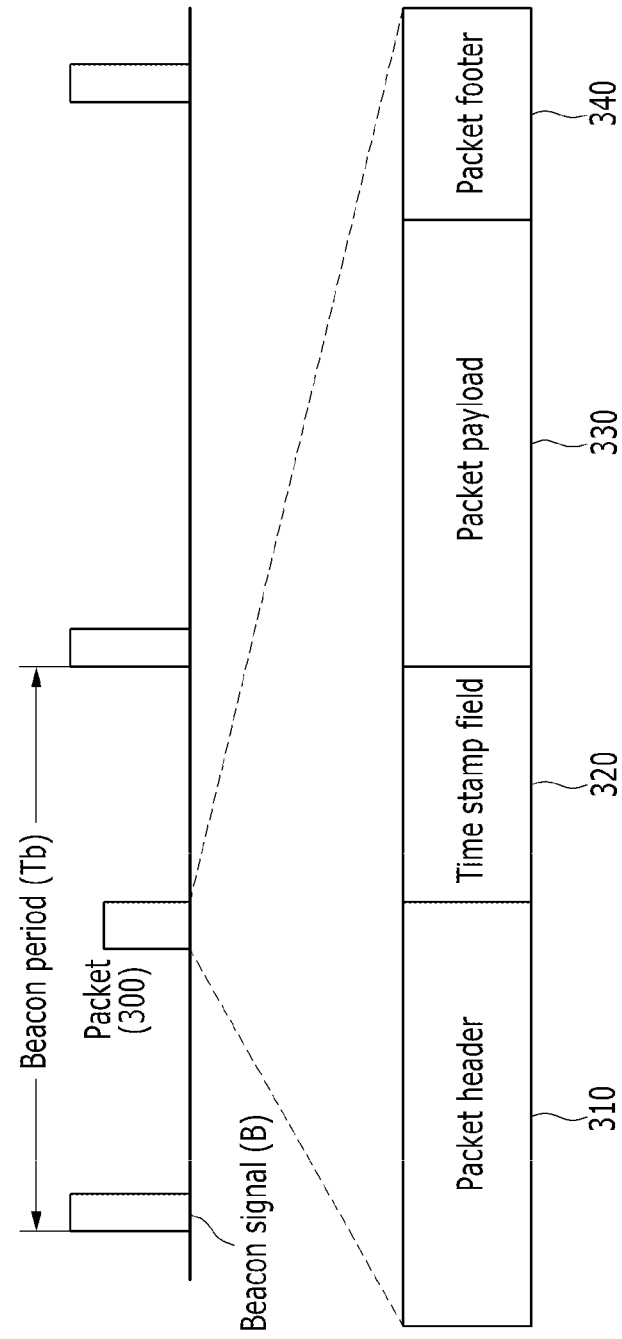
FIG. 3 is a diagram showing a packet including a time stamp field in a beacon period according to the exemplary embodiment of the present invention.

FIG. 3 is a diagram showing the packet including the time stamp field in a beacon period according to the exemplary embodiment of the present invention.

First, the management apparatus 200 transmits the beacon signal B to the sensor apparatus 100 at a predetermined time period Tb to perform synchronization, and receives a packet 300 to transmit the information for a predetermined time period Tb. Herein, the predetermined time period Tb is referred to as a beacon period Tb.

Referring to FIG. 3, the packet 300 includes a packet header 310, a time stamp field 320, a packet payload 330, and a packet footer 340. Herein, the packet header 310, the packet payload 330, and the packet footer 340 correspond to a format of a general packet 300, and a description thereof will be described.

When the sensor 110 is changed from the deactivation state to the activation state, the time stamp field 320 includes a relative value that shows when the biosignal including the bioinformation is transmitted to the management apparatus 200 at any time in the beacon period Tb.

In other words, when the sensor 110 is changed from the deactivation state to the activation state, the sensor apparatus 100 grasps how much time remains until the next beacon signal B is received and determines whether the sensor 110 is to be changed into the deactivation state based on the grasped result.

When a time until the next beacon signal B is to be received is more than a predetermined time, the sensor apparatus 100 changes the operation state of the sensor 110 to the deactivation state.

The relative value represented by the time stamp field 320 according to the exemplary embodiment of the present invention is configured at 8 bits or more. For example, when 8 bits are allocated, the time stamp field 320 includes 256 values. In other words, the time stamp field 320 divides the beacon period Tb into 256 periods and records when the packet is relatively generated in any period.

In the same manner, the information including the relative time period to the time when the packet is generated between the beacon periods is transmitted to a general data frame, and therefore can be used for the time synchronization in which the sensors 110 are changed into the activation state. On the other hand, where there is no information or signal transmitted and received between the management apparatus 200 and the sensor apparatus 100 in the beacon period Tb, the management apparatus 200 generates any packet and uses it as a synchronization signal.

Next, a method for power saving to in-body and on-body communication will be described in detail with reference to FIG. 4.

Figure 4:
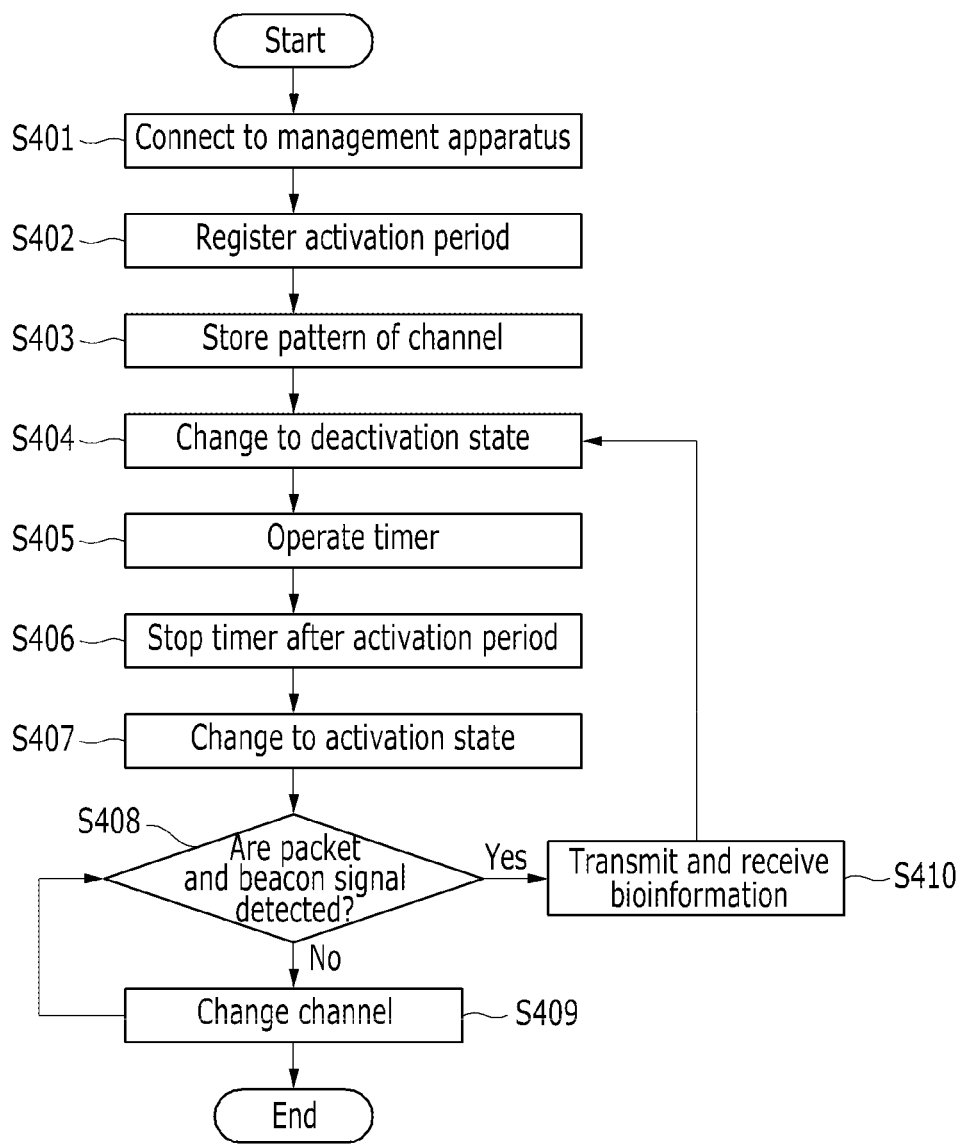
FIG. 4 is a flowchart showing a method for power saving for in-body and on-body communication according to the exemplary embodiment of the present invention.

FIG. 4 is a flowchart showing a method for power saving to in-body and on-body communication according to the exemplary embodiment of the present invention.

First, a system for power saving for in-body and on-body communication includes the plurality of sensor apparatuses 100 and the management apparatus 200. At this time, the sensor apparatus 100 is implanted in-body or is attached on-body to monitor a living body. The operation of the sensor 110 included in the sensor apparatus 100 is classified into an activation state that can sense the bioinformation or an deactivation state in which it is not operated.

Although the exemplary embodiment of the present invention describes the operation scheme based on the packet of the sensor apparatus 100, the time stamp field 320 in the packet is used when the packet is generated in the sensor apparatus 100 as well as is when the control information is transmitted from the management apparatus 200, such that it can be widely used to allow other apparatuses to overhear the timing of packet transmission.

Referring to FIG. 4, the sensor apparatus 100 is connected to the management apparatus 200 when the operation state of the sensor 110 to be monitored is the activation state (S401). At this time, the sensor apparatus 100 and the management apparatus 200 forms the network using tree topology.

When a specific channel for communicating with the management apparatus 200 is formed, the sensor apparatus 100 registers the activation period TPw of the sensor 110 (S402). The activation period TPw means from the time t1 when the sensor 110 is changed from the deactivation state to the activation state to the time t2 when the sensor 110 is again changed from the deactivation state to the activation state. In addition, the activation period TPw includes the first time Tsw that is consumed while changing from the deactivation state to the activation state, the second time Trx that is the activation state, the third time Tws that is consumed while changing from the activation state to the deactivation state, and the fourth time Tsleep that is the deactivation state.

The sensor apparatus 100 stores an inter-channel frequency hopping pattern for moving the channel in order to prevent channel collision when other networks are used for a channel through the communication of the sensor apparatus 100 and the management apparatus 200 (S403). When the operation state of the sensor 110 is changed from the deactivation state to the activation state, the sensor apparatus 100 searches the channel used by the network connected in the previous activation state among the plurality of communication channels.

Next, the sensor apparatus 100 changes the operation state of the sensor 110 to the deactivation state (S404). After the sensor apparatus 100 changes the operation state to the deactivation state, it operates a timer (not shown) (S405).

The sensor apparatus 100 stops the operation of the timer when the activation period TPw is completed during the operation of the timer (S406), and changes the operation state of the sensor 110 to the activation state (S407). After the sensor apparatus 100 changes the operation state to the activation state, it prepares to transmit and receive information.

When the sensor 110 is changed from the deactivation state to the activation state, the sensor apparatus 100 determines whether or not the packet 300 and the beacon signal B are detected during the beacon period Tb (S408).

When the packet 300 and the beacon signal B are not detected, the sensor apparatus 100 changes the channel to correspond to the channel hopping pattern (S409). Next, the sensor apparatus 100 again determines whether or not the packet 300 and the beacon signal B are detected during the beacon period Tb.

When the packet 300 and the beacon signal B are detected, the management apparatus 200 receives the biosignal including the bioinformation at the time when the packet 300 is included and transmits it to the outside (S410). The time when the packet 300 is included is a relative value that shows when other sensor apparatuses transmit the biosignal including the bioinformation to the management apparatus 200 at any time in the beacon period. Next, the sensor apparatus 100 changes the operation state of the sensor 110 to the deactivation state. The sensor apparatus 100 uses minimized power and supplies it, thereby making it possible to save energy.

Next, the timing of detecting the packet 300 and the beacon signal B during the beacon period Tb in the management apparatus 200 in order to save power will be described with reference to FIG. 5.

Figure 5:
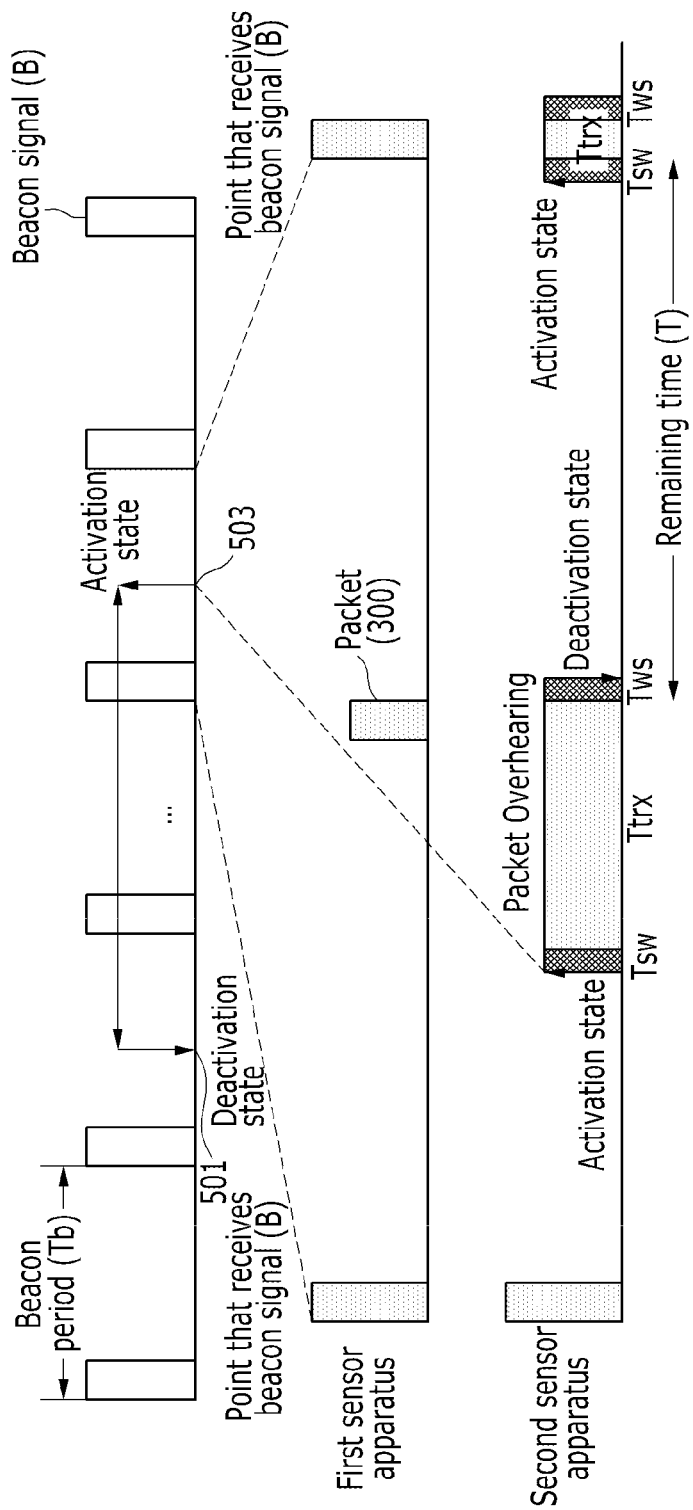
FIG. 5 is a diagram showing timing of detecting the packet and the beacon signal according to the exemplary embodiment of the present invention.

FIG. 5 is a diagram showing timing of detecting the packet and the beacon according to the exemplary embodiment of the present invention.

First, the sensor apparatus 100 maintains the deactivation state as long as possible when there is no bioinformation that will transmit in the operation state and changes the deactivation state to the activation state when there is bioinformation to be transmitted, thereby saving power. To this end, the sensor apparatus 100 obtains information corresponding to the time when the biosignal including the bioinformation can be transmitted in the case where the sensor apparatus 100 is activated during the minimum beacon period Tb. However, when the beacon period Tb is relatively long, it is highly likely to be delayed by a predetermined time until the next beacon signal B is received, when the sensor apparatus 100 is changed into the activation state at any time within the beacon period Tb.

When the sensor apparatus 100 is changed into the activation state after P beacon periods Tb in the state where the operation state of the sensor apparatus 100 is deactivated, it is difficult for the sensor apparatus 100 to determine whether it is changed into the activation state at an accurate time in the beacon period. In particular, since the clock of the sensor apparatus 100 and the management apparatus 200 have different offsets, as the number and length of the beacon periods Tb are increased, it is difficult to grasp the time to change the activation state.

In other words, in the system for saving power, it is necessary to grasp when the operation state is changed in order to reduce the time of maintaining the unnecessary activation state between the beacon period Tb at the time when the sensor apparatus 100 is changed into the activation state.

The sensor apparatus 100 receives the beacon signal B from the management apparatus 200 and transmits the packet 300 including the bioinformation to the management apparatus 200 in the predetermined time period for receiving the beacon signal B, that is, in the beacon period Tb. At this time, the sensor apparatus 100 determines whether the management apparatus 200 receives the biosignal at any time in the beacon period Tb based on the time stamp field 320 of the packet 300, thereby making it possible to determine the operation state of the sensor apparatus 100.

Since the information including the relative value of the time when the packet 300 is generated in the beacon period Tb is transmitted to the general information frame, the same scheme uses the information for the time synchronization, thereby making it possible to change the plurality of sensor apparatuses 100 into the activation state.

The relative value included in the time stamp field 320 is not necessarily the same as the slot time of the beacon period Tb, and represents whether the packet is generated at any position in the beacon period Tb. The sensor apparatus 100 that will be changed into the activation state receives the packet 300 from other apparatuses, and in which beacon period Tb the beacon signal B is transmitted can be appreciated by confirming the time stamp field included in the received packet 300.

Referring to FIG. 5, the first sensor apparatus and the second sensor apparatus, which are included in the plurality of sensor apparatuses 100, will be described.

First, the operation state of the second sensor apparatus is changed from a deactivation state 501 into an activation state 503 after the P beacon periods Tb. At this time, the management apparatus 200 transmits the beacon signal to the plurality of sensor apparatuses 100 at each beacon period Tb to perform synchronization.

When the second sensor apparatus is changed into the activation state 503, it first overhears the packet transmission between peripheral apparatuses. In other words, the second sensor apparatus performs the overhearing until the information frame is generated in other sensor apparatuses, that is, the first sensor apparatus or the management apparatus 200. When the communication between the management apparatus 200 and the first sensor apparatus is generated, the second sensor apparatus detects the packet 300 that is transmitted and received between the management apparatus 200 and the first sensor apparatus to confirm the time stamp field 320 included in the packet 300. Herein, the time stamp field 320 includes the relative value that is shown when the biosignal including the bioinformation is transmitted to the management apparatus 200 at any time in the beacon period Tb when the sensor 110 corresponding to the first sensor apparatus is changed from the deactivation state to the activation state. For this reason, when it knows the entire length of the beacon period Tb, the remaining time T until the next beacon signal is received can be calculated.

When the remaining time T is longer than the third time Tws needed to change the second sensor apparatus from the activation state into the deactivation state and the first time Tsw needed to change the second sensor apparatus from the deactivation state into the activation state, the sensor apparatus returns to the deactivation state to maintain the non-activation state during the remaining time T until the next beacon signal is received. Next, the second sensor apparatus changes the operation state to the activation state prior to the next beacon period and waits to receive the beacon signal B. Through the above process, the time to maintain the operation state of the sensor apparatus 100 in the deactivation state is increased, thereby saving power.

Next, the method for overhearing packets in order to detect the packet 300 and the beacon signal B as shown in FIG. 5 in the method for power saving for in-body and on-body communication will be described in detail with reference to FIG. 6.

Figure 6:
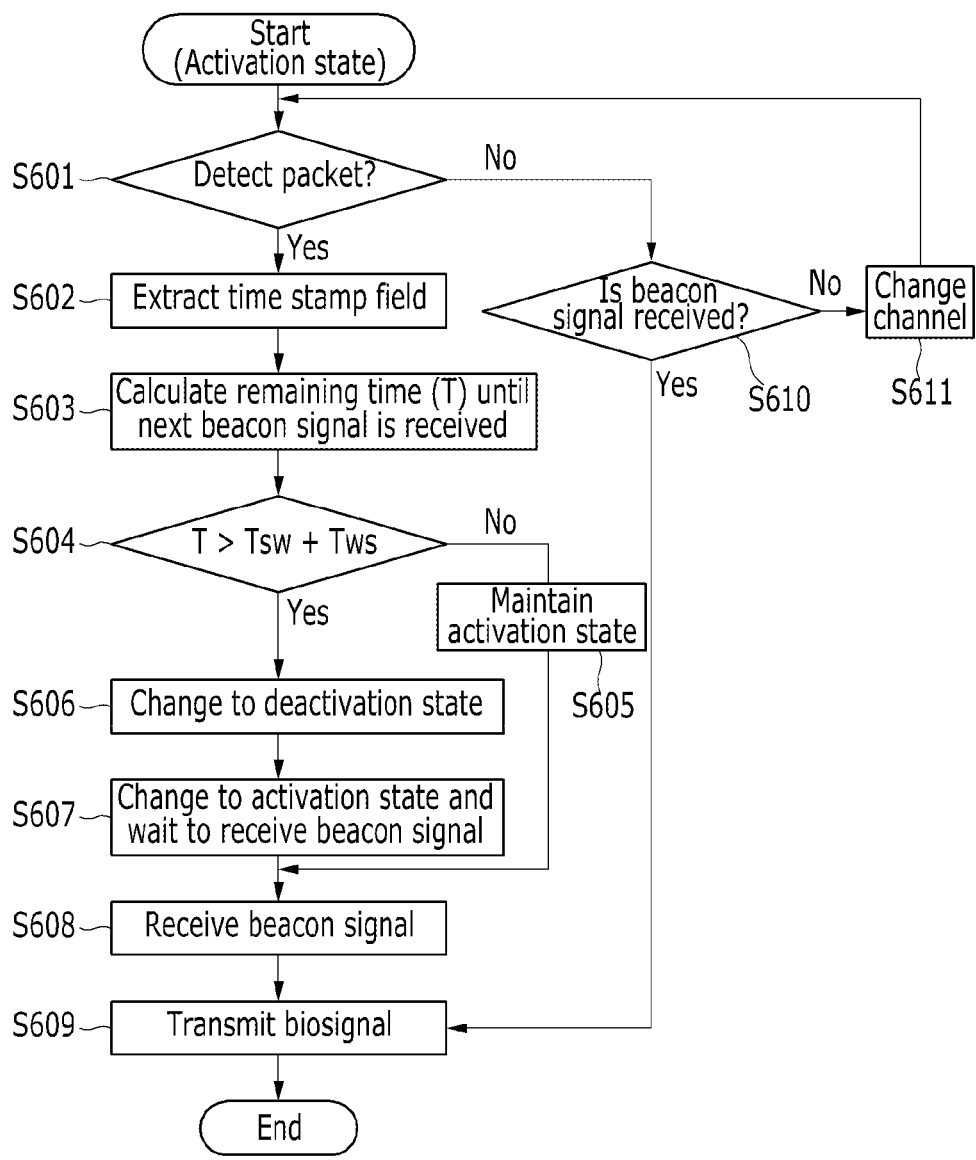
FIG. 6 is a flowchart showing a method for overhearing packets according to an exemplary embodiment of the present invention.

FIG. 6 is a flowchart showing a method for overhearing packets according to an exemplary embodiment of the present invention.

First, the operation state of the sensor apparatus 100 is an activation state.

Referring to FIG. 6, the sensor apparatus 100 determines whether the packet 300 can be detected for the beacon period Tb (S601). When the packet 300 is detected, the sensor apparatus 100 extracts the time stamp field 320 of the detected packet 300 (S602). Next, the sensor apparatus 100 calculates the remaining time T until the next beacon signal is received, based on the extracted time stamp field 320 (S603).

The sensor apparatus 100 compares the remaining time T with a time that that is a sum of the first time Tsw and the third time Tws (S604). Herein, the first time Tsw is a time needed to change the operation state of the sensor apparatus 100 from the deactivation state to the activation state, and the third time Tws is a time needed to change the operation time of the sensor apparatus 100 from the activation state to the deactivation state.

When the time that is a sum of the first time Tsw and the third time Tws is longer, the sensor apparatus 100 maintains the operation state as the activation state (S605). Next, the sensor apparatus 100 detects the beacon signal B.

When the remaining time T is longer, the sensor apparatus 100 changes the operation state from the activation state to the deactivation state and maintains the activation state for the remaining time T until the next beacon signal is received (S606).

The sensor apparatus 100 changes the operation state to the activation state prior to the next beacon period and waits to receive the beacon signal B (S607). If the sensor apparatus 100 receives the next beacon signal B while waiting (S608), it transmits the biosignal including the bioinformation (S609).

When the packet 300 is not detected, the sensor apparatus 100 determines whether the beacon signal B is received (S610). Herein, the sensor apparatus 100 maintains the activation state until the beacon signal B is received.

When the sensor apparatus 100 receives the beacon signal B, it transmits the biosignal including the bioinformation. On the other hand, when the sensor apparatus 100 does not receive the beacon signal B, it changes the channel that performs the communication with the management apparatus 200 (S611). Next, the sensor apparatus 100 back detects the packets through the changed channel.

In other words, the sensor apparatus according to the exemplary embodiment of the present invention always includes the time when the bioinformation in the packet generated in the beacon period and transmits it to the management apparatus, such that other sensor apparatuses can relatively grasp the remaining time until the next beacon signal is received. In this way, other sensor apparatuses are operated in the deactivation state in a period where the transmission and reception of data is not needed, thereby making it possible to reduce the use of power. In addition, apparatuses used in the body communication can use a battery for a long time by reducing power consumption.

The above-mentioned exemplary embodiments of the present invention are not embodied only by an apparatus and method. Alternatively, the above-mentioned exemplary embodiments may be embodied by a program performing functions that correspond to the configuration of the exemplary embodiments of the present invention, or a recording medium on which the program is recorded. These embodiments can be easily devised from the description of the above-mentioned exemplary embodiments by those skilled in the art to which the present invention pertains.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method for power saving in communication between a plurality of sensor apparatuses that are located in-body or on-body to collect bioinformation, and an external management apparatus, comprising:
   connecting a first sensor apparatus to the management apparatus in a state in which the first sensor apparatus monitors a living body;
   registering an activation period of the first sensor apparatus, the activation period comprising a first time to change an operation state of the first sensor apparatus from a deactivation state to an activation state, a second time of the activation state, a third time to change the operation state from the activation state to the deactivation state, and a fourth time of a deactivation state;
   detecting a remaining time until a beacon signal from the management apparatus will be received by the first sensor apparatus;
   comparing the remaining time and a sum of the first time and the third time;
   changing the operation state of the first sensor apparatus from the activation state to the deactivation state when the remaining time is longer than the sum of the first time and the third time, and maintaining the operation state in the activation state when the remaining time is less than the sum;

detecting a packet for a beacon period in the activation state; and transmitting the bioinformation to the management apparatus at the time when the packet is included and changing the operation state of the first sensor apparatus back to the deactivation state.

2. The method for power saving of claim 1, wherein the detecting the packet further includes:

determining whether the beacon signal is detected for the beacon period when the packet is not detected;

determining the operation state of the first sensor apparatus as the activation state when the beacon signal is detected; and connecting the first sensor apparatus to the management apparatus again when the beacon signal is not detected.

3. The method for power saving of claim 1, wherein the detecting the packet includes detecting a packet including the timing when the bioinformation monitored by a second sensor apparatus, not the first sensor apparatus, is transmitted to the management apparatus.

4. The method for power saving of claim 1, wherein the registering the activation period further includes storing a pattern of a specific channel that is formed through the communication with the management apparatus, and wherein the first sensor apparatus searches the specific channel based on the stored pattern and communicates with the management apparatus through the specific channel again when the first sensor apparatus is changed from the deactivation state to the activation state.

5. The method for power saving of claim 1, further comprising performing synchronization by receiving the beacon signal from the management apparatus at each predetermined period, wherein the predetermined period corresponds to the beacon period.

6. A method for power saving in communication between a plurality of sensor apparatuses that are located in-body or on-body to collect bioinformation, and an external management apparatus, comprising:

receiving a first beacon signal from the management apparatus;

detecting a packet in a state in which the sensor apparatus is activated to collect bioinformation;

calculating remaining time until a second beacon signal corresponding to a next signal of a first beacon signal is received, based on a specific field included in the detected packet;

comparing the remaining time with a time that is a sum of a time needed to change the sensor apparatus from the activation state to the deactivation state in which the bioinformation is not collected and a time needed to change the sensor apparatus from the activation state to the deactivation state; and determining the operation state of the sensor apparatus based on the comparison result, including:

changing the operation state of the sensor apparatus from the activation state to the deactivation state when the remaining time is longer than the sum; and maintaining the operation state of the sensor apparatus in the deactivation state for the remaining time until the second beacon signal is received.

7. The method for power saving of claim 6, wherein the determining the operation state of the sensor apparatus includes maintaining the operation state of the sensor apparatus in the activation state when the summed time is longer than the remaining time.

8. The method for power saving of claim 6, further comprising:

determining whether a third beacon signal is received when the sensor apparatus does not detect the packet in the state where the sensor apparatus is activated to collect the bioinformation;

transmitting the bioinformation to the management apparatus when the third beacon signal is received; and changing a channel that performs communication with the management apparatus and detecting the packet when the third beacon signal is not received.

9. A system for power saving in communication with a plurality of sensor apparatuses that are located in-body or on-body to sense bioinformation, comprising:

a management apparatus that performs synchronization by transmitting a beacon signal to the plurality of sensors at each of predetermined periods; and a sensor apparatus that includes a sensor that receives a first beacon signal, grasps how much time remains until the second beacon signal is received when the sensor is activated to sense the bioinformation, determines the operation state of the sensor based on the grasped time through a comparison of the grasped time with a time that is a sum of a time needed to change the sensor from an activation state to a deactivation state and a time needed to change the sensor from the deactivation state to the activation state, and maintains the sensor in the activation state when the summing time is longer.

10. The system for power saving of claim 9, wherein the operation state of the sensor includes the activation state and the deactivation state in which the sensor does not sense the bioinformation, and the sensor uses only necessary power in receiving the beacon signal when the operation state of the sensor is deactivated.

11. The system for power saving of claim 9, wherein the sensor information sensed by the sensor is transmitted to the management apparatus when the second beacon signal is received.

12. The system for power saving of claim 9, wherein the sensor is maintained in the deactivation state until the second beacon signal is received by changing the operation state of the sensor from the activation state to the deactivation state when the grasped time is longer than the sum.

* * * * *